(12) United States Patent
Calderoni et al.

(10) Patent No.: US 10,542,976 B2
(45) Date of Patent: Jan. 28, 2020

(54) POWERED SURGICAL INSTRUMENT WITH PRESSURE SENSITIVE MOTOR SPEED CONTROL

(71) Applicant: Covidien LP, Mansfield, MA (US)

(72) Inventors: Anthony Calderoni, Bristol, CT (US); Xingrui Chen, Glastonbury, CT (US); Luis Dussan, East Haven, CT (US); John Pantazis, Stratford, CT (US); Japhet Colon, New Haven, CT (US)

(73) Assignee: Covidien LP, Mansfield, MA (US)

( * ) Notice: Subject to any disclaimer, the term of this patent is extended or adjusted under 35 U.S.C. 154(b) by 629 days.

(21) Appl. No.: 14/730,662

(22) Filed: Jun. 4, 2015

(65) Prior Publication Data

US 2016/0030040 A1 Feb. 4, 2016

Related U.S. Application Data (60) Provisional application No. 62/031,340, filed on Jul. 31, 2014.

(51) Int. Cl.
*A61B 17/072* (2006.01)
*H01H 13/50* (2006.01)
(Continued)

(52) U.S. Cl.
CPC .......... *A61B 17/072* (2013.01); *H01H 13/50* (2013.01); *H02P 31/00* (2013.01);
(Continued)

(58) Field of Classification Search
CPC ............ A61B 17/072; A61B 17/07207; A61B 2017/00017; A61B 2017/00137; A61B 2017/00203; A61B 2017/00371; A61B 2017/00389; A61B 2017/00393; A61B 2017/00398; A61B 2017/00477; A61B 2017/07257; A61B 2017/07271; A61B 2017/07285; H01H 13/50; H02P 31/00
(Continued)

(56) References Cited

U.S. PATENT DOCUMENTS

| 4,705,038 A | 11/1987 | Sjostrom et al. | |
| 5,717,176 A * | 2/1998 | Dahlstrom | H01H 13/64 200/1 B |

(Continued)

OTHER PUBLICATIONS

European Search Report dated Dec. 8, 2015, issued in EP Application No. 15179003.

(Continued)

*Primary Examiner* — Alexander M Valvis
*Assistant Examiner* — Mary C Hibbert-Copeland (57) ABSTRACT

A surgical instrument includes a drive shaft, a motor for rotating the drive shaft, and a motor speed control. The motor speed control includes a first switch and a second switch which are in communication with the motor. The first switch is disposed over and in registration with the second switch. The first switch has an activated state such that the first switch sends a first signal to the motor. The motor rotates the drive shaft in response to the first signal. The second switch sends a second signal to the motor that varies the speed that the motor rotates the drive shaft in response to a force applied to the second switch by the first switch.

13 Claims, 5 Drawing Sheets

(51) Int. Cl.
*H02P 31/00* (2006.01)
*A61B 17/00* (2006.01)

(52) U.S. Cl.
CPC ............... *A61B 2017/00203* (2013.01); *A61B 2017/00371* (2013.01); *A61B 2017/00393* (2013.01); *A61B 2017/00477* (2013.01); *A61B 2017/07257* (2013.01); *A61B 2017/07271* (2013.01); *A61B 2017/07285* (2013.01)

(58) Field of Classification Search
USPC .................. 227/175.1–176.1; 606/1, 180
See application file for complete search history.

(56) References Cited

U.S. PATENT DOCUMENTS

| | | | |
|---|---|---|---|
| 7,422,139 B2 | 9/2008 | Shelton, IV et al. | |
| 7,481,347 B2 | 1/2009 | Roy | |
| 8,573,465 B2 | 11/2013 | Shelton, IV | |
| 2011/0204119 A1 | 8/2011 | McCuen | |
| 2012/0089131 A1 | 4/2012 | Zemlok et al. | |
| 2012/0253329 A1 | 10/2012 | Zemlok et al. | |
| 2013/0046290 A1 | 2/2013 | Palmer et al. | |
| 2013/0126581 A1 | 5/2013 | Yates et al. | |
| 2013/0181034 A1 | 7/2013 | Shelton, IV et al. | |
| 2013/0313304 A1* | 11/2013 | Shelton, IV | A61B 17/072 227/176.1 |
| 2014/0232316 A1* | 8/2014 | Philipp | A61B 17/151 318/504 |

OTHER PUBLICATIONS

Chinese Office Action dated Sep. 3, 2018, issued in CN Appln. No. 2015104611988.

EP Office Action for application No. 15 179 003.7 dated May 10, 2019.

* cited by examiner

POWERED SURGICAL INSTRUMENT WITH PRESSURE SENSITIVE MOTOR SPEED CONTROL

CROSS-REFERENCE TO RELATED APPLICATIONS

This application claims the benefit of and priority to U.S. Provisional Patent Application No. 62/031,340, filed Jul. 31, 2014, the entire disclosure of which is incorporated by reference herein.

BACKGROUND

1. Technical Field

The present disclosure relates to surgical instruments and, more specifically, to speed control systems for powered surgical instruments.

2. Discussion of Related Art

A number of surgical device manufacturers have developed product lines with proprietary drive systems for operating or manipulating the surgical device. In many instances the surgical devices include a handle assembly, which is reusable, and a disposable end effector or the like that is selectively connected to the handle assembly prior to use and then disconnected from the handle assembly following use in order to be disposed of or in some instances sterilized for re-use.

Many of the existing end effectors for use with many of the existing surgical devices or handle assemblies linearly advance a firing assembly to actuate the end effector. For example, end effectors for performing endo-gastrointestinal anastomosis procedures, end-to-end anastomosis procedures, and transverse anastomosis procedures, each typically require a linear advancement of a firing assembly in order to be operated.

Existing handle assemblies advance the firing assemblies at a predetermined speed. In addition, some handle assemblies include feedback systems that reduce the predetermined speed in response to surgical conditions such as tissue thickness. However, a clinician using the surgical device lacks control of the firing speed of the handle assembly.

Accordingly, there is a need to provide a clinician with an ability to vary the speed of advancement a firing assembly based surgical conditions observed by the clinician.

SUMMARY

In an aspect of the present disclosure, a surgical instrument includes a drive shaft, a motor for rotating the drive shaft and a motor speed control. The motor speed control includes a first switch and a second switch which are each in communication with the motor. The first switch is disposed over and in registration with the second switch. The first switch has an activated state such that the first switch sends a first signal to the motor. The motor rotates the drive shaft in response to the first signal. The second switch sends a second signal to the motor that varies the speed that the motor rotates the drive shaft in response to a force applied to the first switch.

In aspects, the second switch includes a force sensitive resistor that generates the second signal in response to the force applied to the first switch.

In some aspects, the motor rotates the drive shaft at a first radial speed in response to the first signal and rotates the drive shaft at a second radial speed in response to the second signal, the second radial speed being different than the first radial speed. The second radial speed may vary in response to a strength of the second signal. The strength of the second signal may vary in response to the force applied to the first switch. The strength of the second signal may vary proportionally or exponentially to the force applied to the first switch. The strength of the second signal may increase as the force applied to the first switch increases.

In certain aspects, the surgical instrument includes a first button slidably disposed over the motor speed control such that as the first button is depressed, the first button engages the first switch. The first button may apply the force to the first button. The first and second switches may be integrally formed as a tactile dome switch.

In another aspect of the present disclosure, a method of controlling the actuation speed of an end effector of a surgical instrument includes activating a first switch and applying a second force to the first switch. Activating the first switch includes sending a first signal to a motor by applying a first force to the first switch. The motor rotates a drive shaft at a first radial speed in response to the first signal. The drive shaft is operatively associated with an end effector of the surgical instrument to actuate the end effector. Applying the second force to the first switch includes the first switch applying a pressure to a second switch disposed under the first switch. The second switch sends a second signal to the motor which rotates the drive shaft at a second radial speed in response to the second signal. The second radial speed is different from the first radial speed.

In aspects, the method includes depressing a button that engages the first switch to activate the first switch and to apply the second force to the first switch.

In some aspects, actuating the end effector includes moving jaw members of the end effector from an open position to a clamped position. Additionally or alternatively, actuating the end effector may include ejecting staples from a jaw member of the end effector.

In certain aspects, actuating the end effector includes advancing a knife through a jaw member of the end effector.

In particular aspects, applying the first force to the first switch includes depressing the first switch a first distance and applying the second force may include depressing the first switch a second distance beyond the first distance.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

Figure 1:
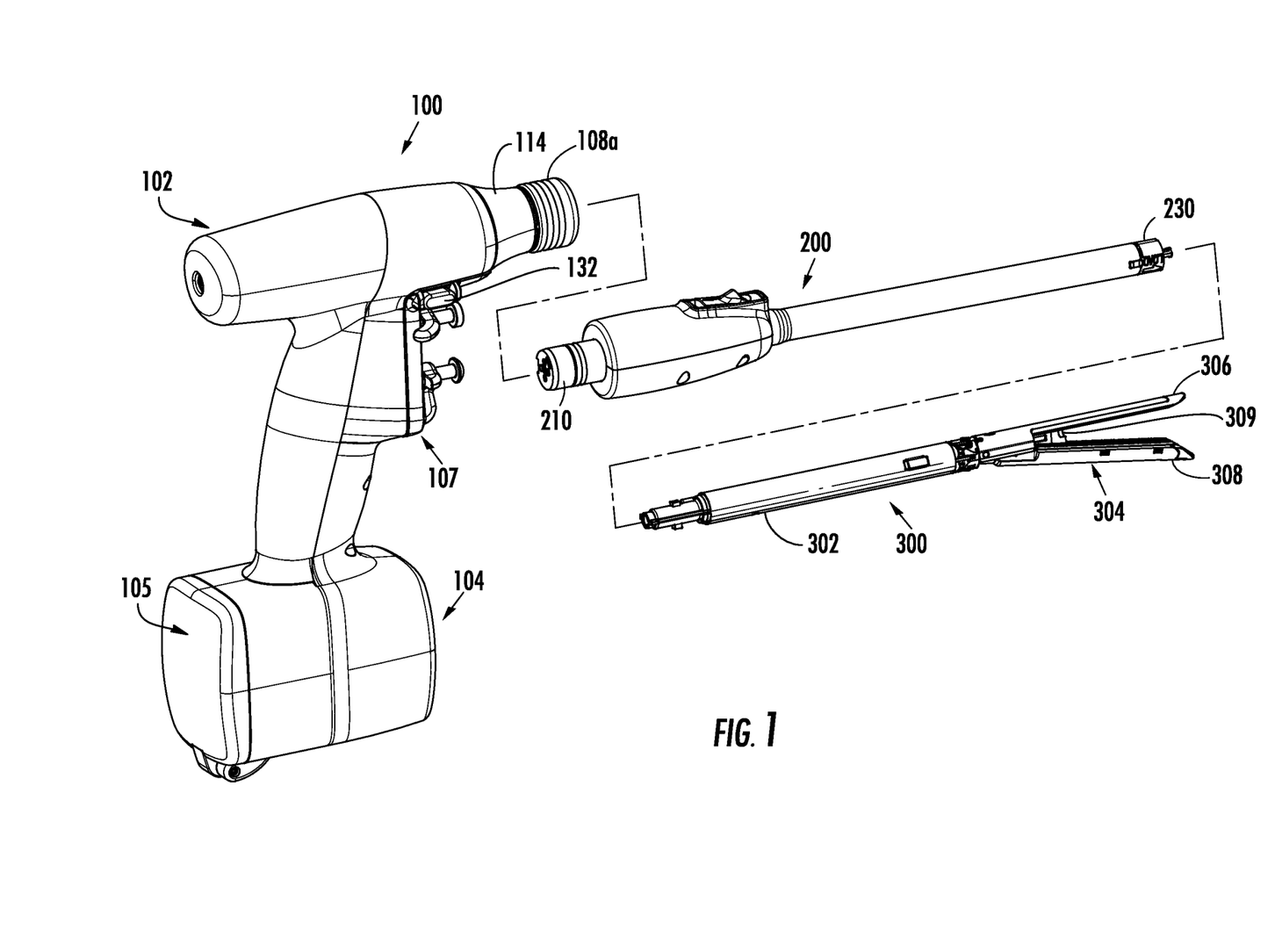
FIG. 1 is a perspective view, with parts separated, of a surgical instrument and adapter, in accordance with an embodiment of the present disclosure, illustrating a connection thereof with an end effector.

As illustrated in FIG. 1, surgical device 100 is configured for selective connection with an adapter 200, and, in turn, adapter 200 is configured for selective connection with an end effector or single use loading unit 300. As detailed herein, end effector 300 is a stapling end effector; however, it is contemplated that the surgical device 100 may be selectively connected to a plurality of end effectors that are configured to perform a variety of surgical procedures to tissue (e.g., stapling, sealing, dissecting, and sampling).

Figure 2:
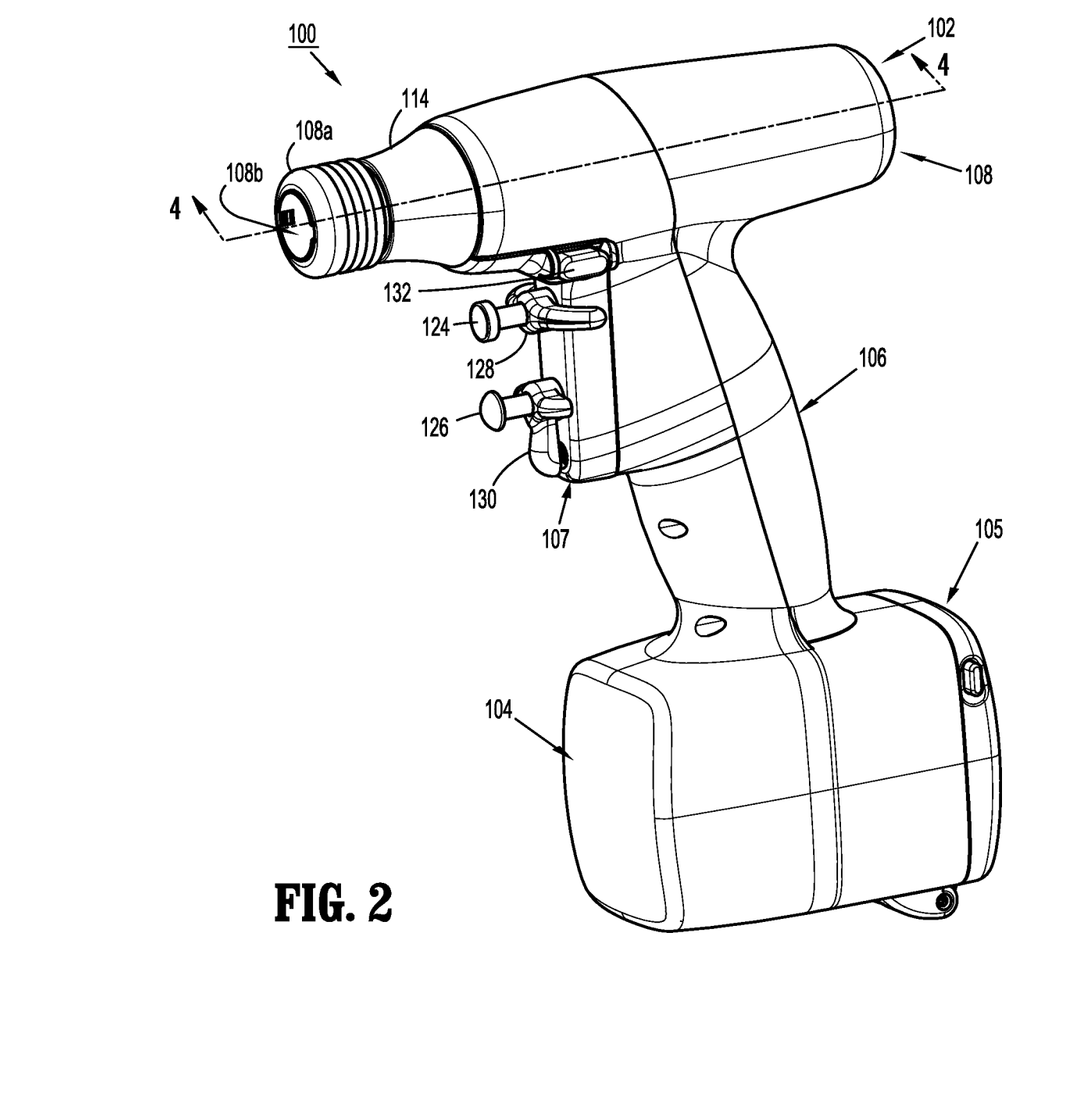
FIG. 2 is a perspective view of the surgical instrument of FIG. 1.
Figure 3:
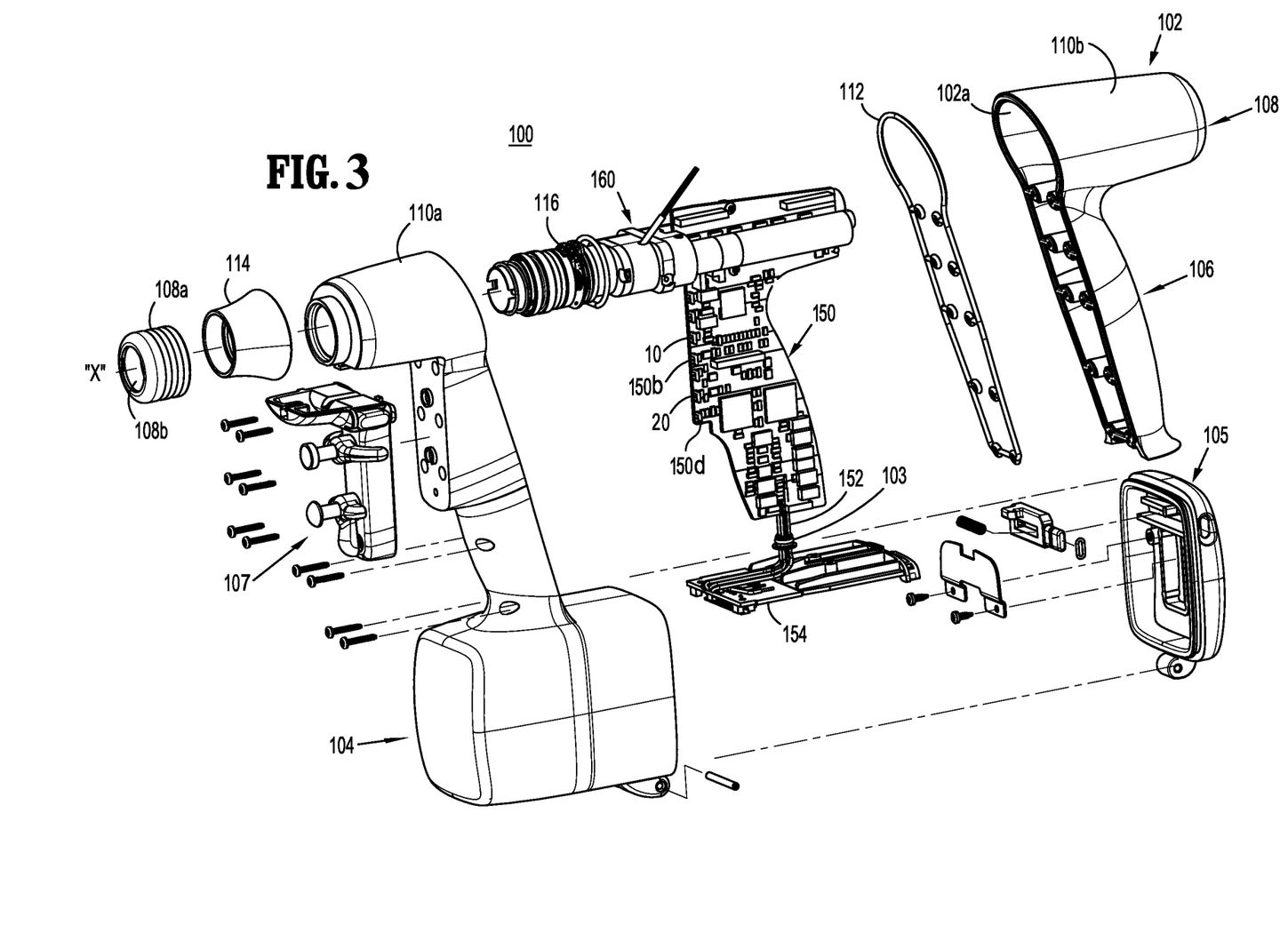
FIG. 3 is a perspective view, with parts separated, of the surgical instrument of FIGS. 1 and 2.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Upper housing portion 108 of handle housing 102 provides a housing in which drive mechanism 160 is situated. The drive mechanism 160 is configured to drive shafts and/or gear components in order to perform the various operations of surgical device 100. In particular, drive mechanism 160 is configured to drive shafts and/or gear components in order to selectively move tool assembly 304 of end effector 300 (FIG. 1) relative to proximal body portion 302 of end effector 300, to rotate end effector 300 about a longitudinal axis "X" (FIG. 3) relative to handle housing 102, to move anvil assembly 306 relative to cartridge assembly 308 of end effector 300 between open and clamped positions, or to fire a stapling and cutting cartridge within cartridge assembly 308 of end effector 300 to eject staples (not explicitly shown) from the cartridge assembly 308 and to advance a knife 309 through the cartridge assembly 308.

The drive assembly 160 includes a first motor 80 that rotates a first drive shaft 82 and a second motor 90 that rotates a second drive shaft 92. The first drive shaft 82 is operatively associated with the end effector 300 such that rotation of the first drive shaft 82 fires stapling and cutting cartridge within the cartridge assembly 308. The second drive shaft 92 is operatively associated with the end effector 200 such that rotation of the second drive shaft rotates the end effector 200 about the longitudinal axis "X" as detailed below. It is contemplated that the first and second drive shafts 82, 92 may be operatively associated with different functions of the end effector 200.

Exemplary examples of electromechanical, hand-held, powered surgical instruments and adapters are disclosed in commonly owned and co-pending U.S. patent application Ser. No. 13/331,047, filed Dec. 20, 2011 and published as U.S. Patent Publication No. 2012/0089131 on Apr. 12, 2012, and Ser. No. 13/484,975, filed May 31, 2012 and published as U.S. Patent Publication No. 2012/0253329 on Oct. 4, 2012, the contents of each are hereby incorporated by reference in their entirety.

As illustrated in FIGS. 1-3, the handle housing 102 supports a trigger housing 107 on a distal surface or side of the intermediate housing portion 108. The trigger housing 107, in cooperation with the intermediate housing portion 108, supports a pair of finger-actuated control buttons 124, 126 and rocker devices 128, 130. In particular, the trigger housing 107 defines an upper aperture 125 for slidably receiving a first control button 124, and a lower aperture 127 for slidably receiving a second control button 126. Each one of the control buttons 124, 126 is moved or actuated by a clinician to affect movement of the end effector 300.

Figures 4, 5, 6:
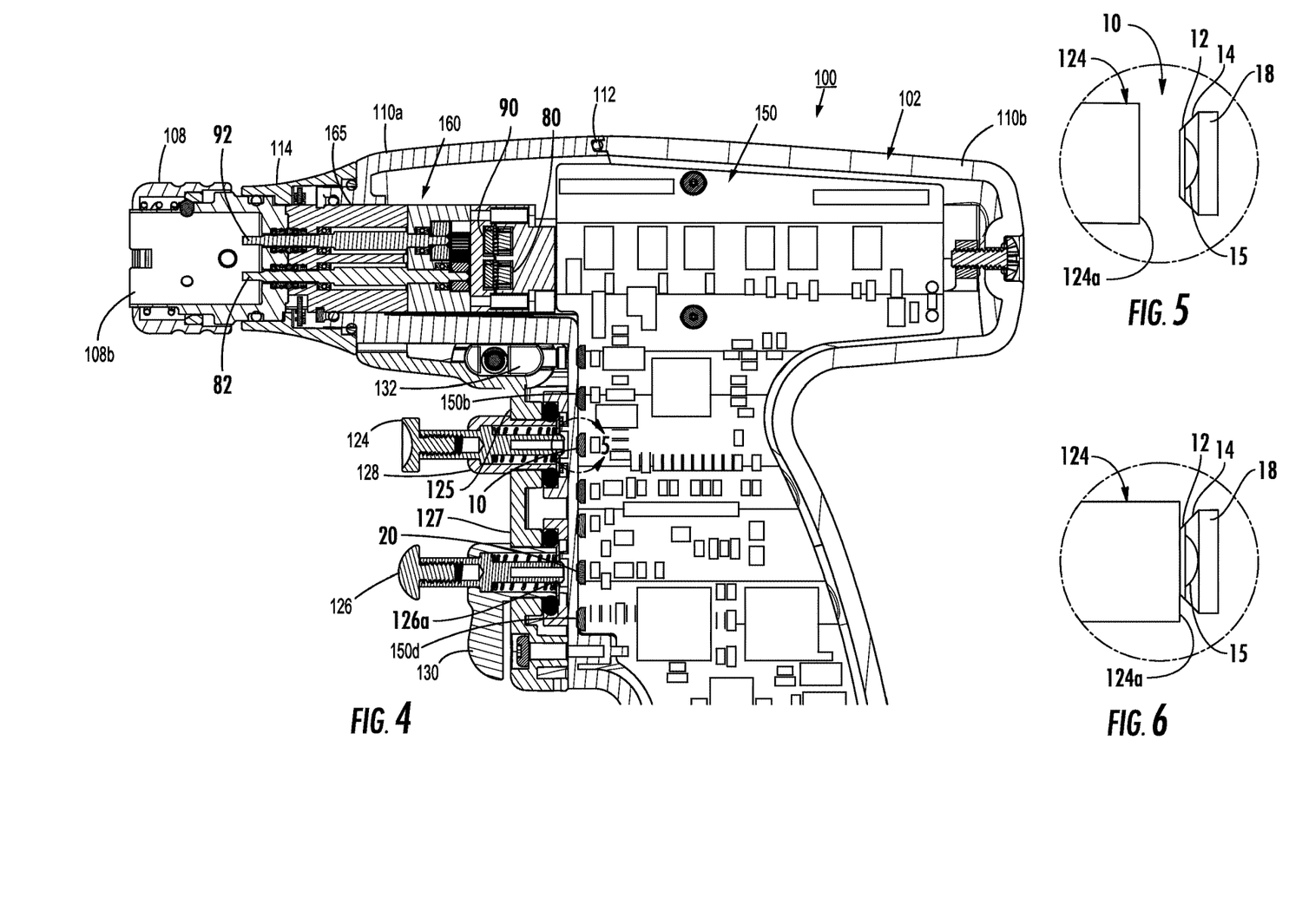
FIG. 4 is a cross-sectional view taken along the section line 4-4 of FIG. 2.
FIG. 5 is an enlarged view of the area of detail of FIG. 4.
FIG. 6 is a side view of the motor speed control with the button engaging the motor speed control.

With additional reference to FIGS. 4-6, the circuit board 150 includes motor speed controls 10, 20 that are engaged by the control buttons 124, 126 to affect movement of the end effector 300. Each of the motor speed controls 10, 20 are in communication with the drive assembly 160 to affect rotation of the first and second drive shafts 82, 92. The motor speed control 10 is in communication with the motor 80 to control the rotational speed of first drive shaft 82 and the motor speed control 20 is in communication with the motor 90 to control the rotational speed of the second drive shaft 92.

Each of the control buttons 124, 126 includes a plunger 124a, 126a that engages a respective one of the motor speed controls 10, 20. With particular reference to FIGS. 5 and 6, the motor speed control 10 is located immediately proximal to the control button 124 and is engagable by the plunger 124a of the control button 124.

The motor speed control 10 includes a first switch 12, a second switch 14, and a control support 18. The control support 18 is fixed to the circuit board 150 and supports the first and second switches 12, 14 on a distal facing surface directed towards the plunger 124a. The second switch 14 is mounted on the control support 18 between the first switch 12 and the control support 18. The control button 124 is depressible a first distance to engage the first switch 12 with a plunger 124a of the control button 124. When the plunger 124a engages the first switch 12, the first switch 12 applies a force or pressure to the second switch 14. It is contemplated that the first and second switches 12, 14 may be provided as a tactile dome switch such that the first and second switches are integrally formed with one another.

When the first switch 12 is activated by the plunger 124a, the motor speed control 10 sends a first signal $S_1$ (FIG. 7) to the motor 80. The first signal $S_1$ activates the motor 80 to rotate the first drive shaft 82 at a first radial speed. The first switch 12 may have a threshold pressure that is required to activate the first switch 12.

When the first switch 12 is activated, any additional force applied to the first switch 12, beyond an initial activation amount of the first switch 12, is transferred to the second switch 14 (i.e., when the first switch is depressed a second distance after the first distance). The second switch 14 includes a force resistor 15 that detects the force or pressure applied to the second switch 14 by the first switch 12 and sends a second signal $S_2$ (FIG. 7) that controls the rotational speed of the first motor 80. As the force applied to the control button 124 is increased, the force applied to the first switch 12 by the plunger 124a is increased, and thus, the force applied to the second switch 14, by the first switch 12, is increased. As the force applied to the second switch is increased, the force resistor 15 increases the strength of the second signal $S_2$. As the strength of the second signal $S_2$ increases, the rotational speed of the first motor 80 increases such that the first drive shaft 82 rotates at a second radial speed that is greater than the first radial speed. It will be appreciated that as the force applied to the force resistor 15 increases, the speed at which the first motor 80 rotates the first drive shaft 82 increases.

It is contemplated that the speed at which the first motor 80 rotates the first drive shaft 82 increases proportionally to the increase in the force realized by the force resistor 15. Alternatively, it is contemplated that the speed at which the first motor 80 rotates the first drive shaft 82 increases exponentially to the increase in the force realized by the force resistor 15. In addition, it is contemplated that as the force realized by the force resistor 15 increases, the speed at which the first motor 80 rotates the first drive shaft 82 decreases.

The second motor control 20 is operatively associated with a second motor 90 that rotates a second drive shaft 92. The second motor control 20 is engaged by the second switch 126 and controls the second motor 90 in a manner similar to the first motor control 10 controlling the first motor 80 detailed above. Accordingly, the operation of the second switch 126 and the second motor control 20 will not be detailed herein for reasons of brevity.

It is contemplated that the first motor speed control 10 and/or the second motor speed control 20 is provided on an external surface of the surgical instrument 100 such that the motor speed controls 10, 20 may be directly engaged by a clinician (e.g., a clinician may directly engage the first switch 12 and apply increased pressure to the first switch 12 to increase the speed of a motor associated with the first motor speed control 10).

Figure 7:
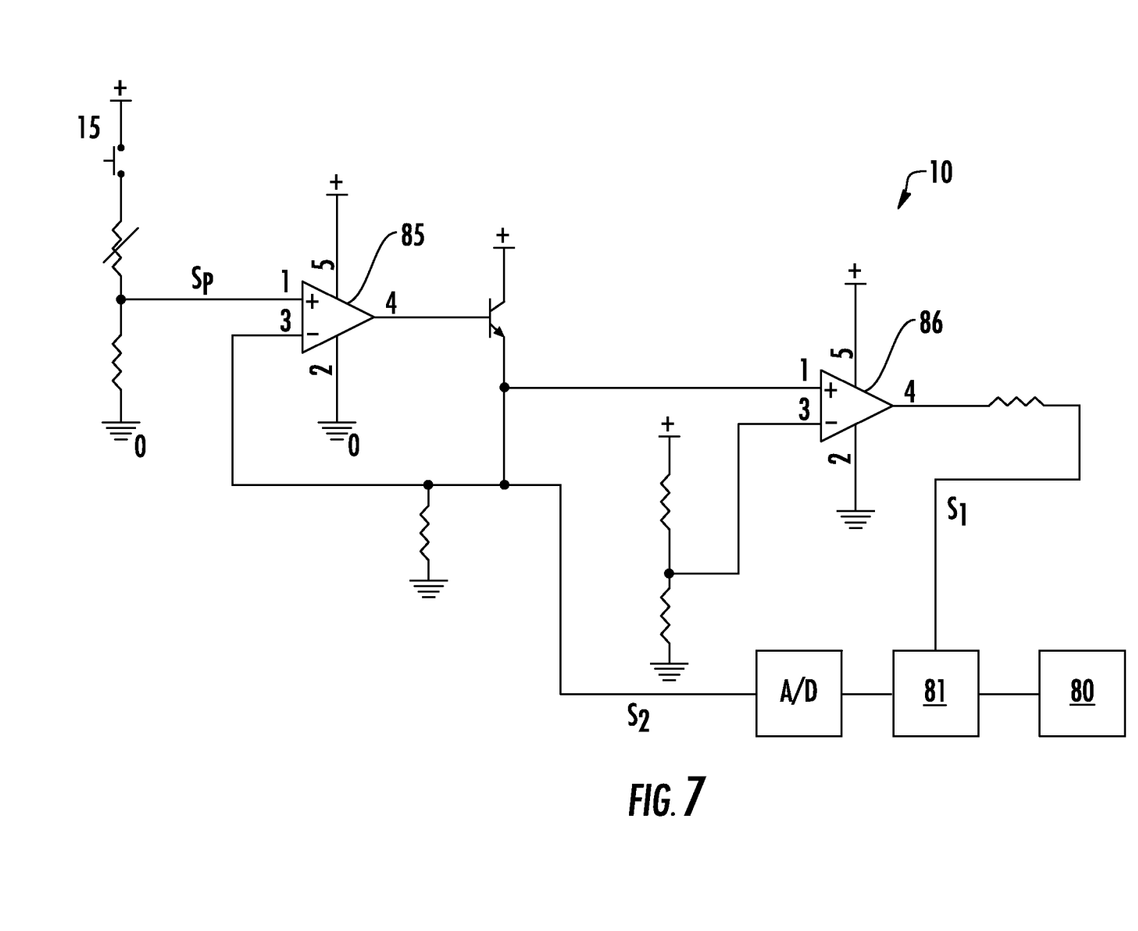
FIG. 7 is a schematic view of an exemplary electrical circuit of the motor speed control of FIG. 4 in accordance with the present disclosure.

Referring to FIG. 7, when the first switch 12 is activated, the first signal $S_1$ is sent from a second op amp 86 to a motor control unit 81 that is in electrical communication with the motor 80 to power the motor 80. The first signal $S_1$ is a binary signal (e.g., on or off) such that when the first signal $S_1$ activates the motor 80 by supplying energy to the motor 80 such that the motor 80 rotates at the first radial speed. When the second switch 14 is depressed, the force resistor 15, which is disposed within the second switch 14, increases the strength of the second signal $S_2$ sent to a first op amp 85. The second signal $S_2$ is sent from the first op amp 85 to the motor control 81 which supplies energy to the motor 80 in response to the second signal $S_2$ such that the radial speed of the motor 80 changes in response to the second signal $S_2$.

In an embodiment, as the first switch 12 is depressed, the force resistor 15 sends a pressure signal Sp to the first op amp 85 that is proportional to the pressure applied to the first switch 12. When the pressure signal Sp is over or greater than a threshold value (i.e., the pressure on the force resistor 15 is over or greater than a threshold value), the first op amp 85 activates the second op amp 86 to send the first signal $S_1$ to the motor control 81. The first op amp 85 also sends the second signal $S_2$ to the motor control 81 that is proportional to the pressure signal Sp. The second signal $S_2$ may pass through an analog to digital converter between the first op amp 85 and the motor control 81.

It some embodiments, the first signal $S_1$ is a bi-stable signal that can be used either for two speed motor control (e.g., high and low) or could be used as a range switch for setting the motor 80 in a variable low speed range or a variable high speed range.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument comprising:
    a drive shaft;
    at least one drive mechanism operatively connected to the drive shaft, the at least one drive mechanism being configured to selectively move a tool assembly of an end effector relative to a proximal portion of the end effector, to rotate the end effector about a longitudinal axis relative to a handle housing, or to move an anvil assembly relative to a cartridge assembly of the end effector between open and clamped positions;
    a motor for actuating the drive shaft via the drive mechanism;
    a motor speed control including a first switch and a second switch, each of the first and second switches in communication with the motor, the first switch disposed over the second switch and in registration therewith, the first switch having an activated state when a force applied to the first switch exceeds a threshold force, wherein the first switch sends a first signal to the motor such that the motor rotates the drive shaft at a constant speed, the second switch sending a second signal to the motor that varies the speed that the motor rotates the drive shaft in response to an amount of the force applied to the first switch which exceeds the threshold force; and
    a force resistor disposed within the second switch and configured to send a pressure signal to a first op amp, such that when the pressure signal is greater than a threshold value the first op amp activates a second op amp to send the first signal to the motor speed control configured to supply energy to the motor, while simultaneously sending a second signal that is proportional to the pressure signal to the motor speed control, such that the second signal to the motor varies the speed that the motor rotates the drive shaft in response to an amount of the force applied to the first switch which exceeds the threshold force.

2. The surgical instrument of claim 1, wherein the second switch includes a force sensitive resistor that generates the second signal in response to the force applied to the first switch.

3. The surgical instrument of claim 1, wherein the motor is adapted to rotate the drive shaft at a first radial speed in response to the first signal and rotates the drive shaft at a second radial speed in response to the second signal, the second radial speed being different than the first radial speed.

4. The surgical instrument of claim 3, wherein the motor is adapted to vary the second radial speed in response to a strength of the second signal.

5. The surgical instrument of claim 4, wherein the strength of the second signal varies in response to the force applied to the first switch.

6. The surgical instrument of claim 5, wherein the strength of the second signal varies proportionally to the force applied to the first switch.

7. The surgical instrument of claim 5, wherein the strength of the second signal varies exponentially to the force applied to the first switch.

8. The surgical instrument of claim 5, wherein the strength of the second signal increases as the force applied to the first switch increases.

9. The surgical instrument of claim 1, further comprising a first button slidably disposed over the motor speed control such that as the first button is depressed, the first button engages the first switch.

10. The surgical instrument of claim 1, wherein the first and second switches are integrally formed as a tactile dome switch.

11. The surgical instrument of claim 1, wherein the first switch is configured to continuously send the first signal to the motor when the first switch is in the activated state.

12. The surgical instrument of claim 1, wherein the second switch is configured to send the second signal to the motor as the first switch sends the first signal to the motor.

13. The surgical instrument of claim 1, wherein the motor is configured to simultaneously receive the first and second signals.

* * * * *